United States Patent [19]

Henderson

[11] 4,326,533
[45] Apr. 27, 1982

[54] COOLANT BAND

[76] Inventor: Mary M. Henderson, 4401 Tyne Blvd., Nashville, Tenn. 37215

[21] Appl. No.: 88,848

[22] Filed: Oct. 29, 1979

Related U.S. Application Data

[62] Division of Ser. No. 867,582, Jan. 6, 1978, Pat. No. 4,204,543.

[51] Int. Cl.³ .............................................. A61F 7/00
[52] U.S. Cl. .................................... 128/402; 128/403; 150/2.3
[58] Field of Search ............... 128/380, 381, 402, 403; 2/7, 171.2, 181, 181.2, 181.8, 182.2, 182.3, 182.5, 182.7; 150/2.2, 2.3, 2.6

[56] References Cited

U.S. PATENT DOCUMENTS

| | | | |
|---|---|---|---|
| 1,473,506 | 11/1923 | Nessler | 128/402 X |
| 1,567,931 | 12/1925 | Epler | 150/2.6 X |
| 1,927,751 | 9/1933 | Mensi | 150/2.2 |
| 1,964,962 | 7/1934 | Rosenblum | 150/2.2 X |
| 2,769,308 | 11/1956 | Krasno | 2/171.2 |
| 2,984,839 | 5/1961 | Conrad et al. | 2/7 |
| 3,149,943 | 9/1964 | Amador | 128/403 X |
| 3,500,014 | 3/1970 | Longo | 128/402 X |
| 3,506,013 | 4/1970 | Zdenek | 128/402 |
| 3,889,684 | 6/1975 | Lebold | 128/402 |
| 3,900,035 | 8/1975 | Welch et al. | 128/402 |
| 3,950,789 | 4/1976 | Konz et al. | 128/402 X |
| 4,055,188 | 10/1977 | Pelton | 128/402 |
| 4,068,318 | 1/1978 | McMahon | 273/29 A X |
| 4,081,150 | 3/1978 | Tyson | 128/402 |

FOREIGN PATENT DOCUMENTS 460200  1/1937  United Kingdom ............... 128/402

Primary Examiner—Richard J. Apley

[57] ABSTRACT

A band of textile material is disclosed containing a pocket with an opening for receiving and storing a bag of freezable liquid or semi-liquid material. The band has an elastic or adjustable means associated with it for maintaining the pocket and the bag contained therein in direct contractive engagement with the part of the anatomy to be cooled.

3 Claims, 8 Drawing Figures

U.S. Patent    Apr. 27, 1982    4,326,533
FIG. 1
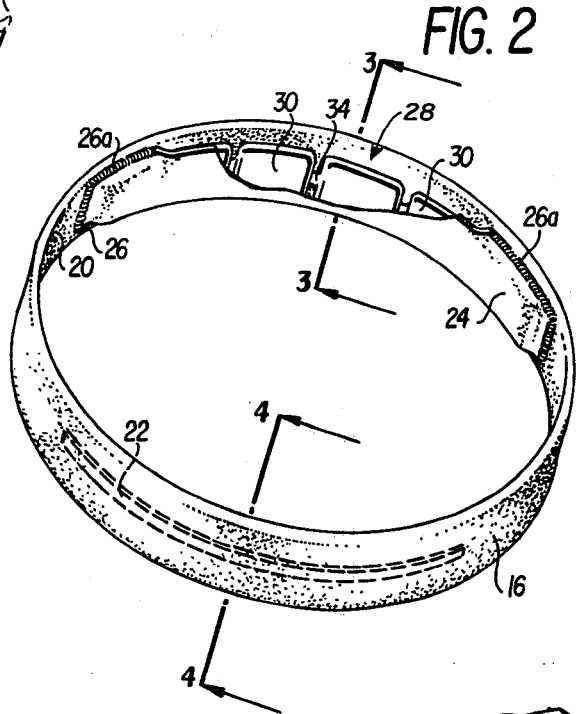
FIG. 2
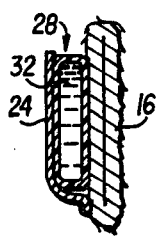
FIG. 3
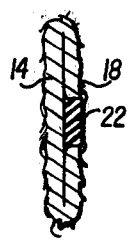
FIG. 4
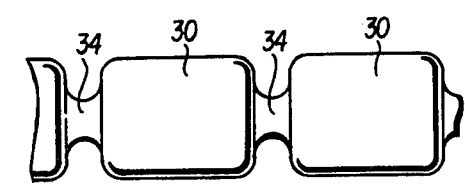
FIG. 5
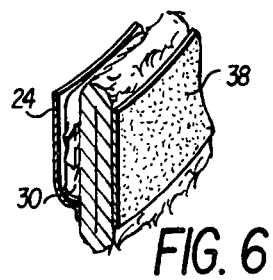
FIG. 6
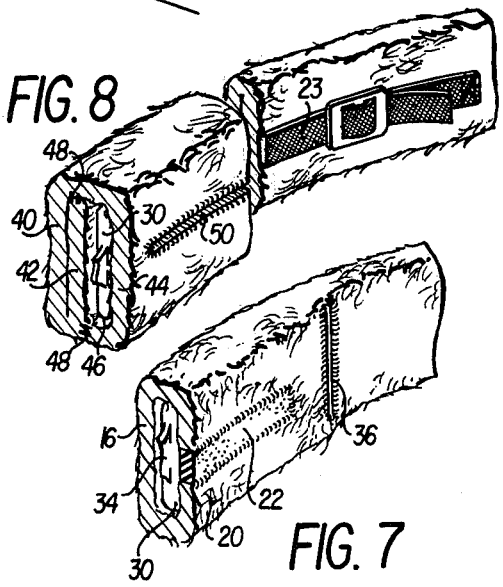
FIG. 8
FIG. 7

COOLANT BAND

This is a division of application Ser. No. 867,582, filed Jan. 6, 1978 now U.S. Pat. No. 4,204,543.

BACKGROUND OF THE INVENTION

This invention relates generally to body cooling devices and more specifically to an elasticized or adjustable band of cloth material to be worn on the body having at least one pocket for receiving and storing a container of frozen liquid or semi-liquid material.

Body coolant devices having compartments containing ice are not new, for example, U.S. Pat. No. 1,567,931 discloses a compress having a pocket which can be filled with ice or hot or cold water for use in relieving pain or inflammation. Similarly, in U.S. Pat. No. 1,569,877 a closed end tubular container lined with waterproof material is taught having a plurality of separate compartments arranged in series each of which can be filled with ice and wrapped around the head or body of a person to cool same. These devices have the common disadvantage that the compartment receiving the coolant must be made of a separate waterproof material and be sufficiently large to accommodate ice in cube or enlarged crushed form thus rendering the device bulky, heavy and generally uncomfortable to wear. Filling such compartments with ice and removing and cleaning same after the ice melts is also a time consuming and messy procedure.

Other types of devices for cooling various parts of the body are disclosed in U.S. Pats. Nos. 3,506,013 and 3,900,035 wherein bandages are disclosed having bags containing a freezable liquid permanently enclosed in a textile material. These devices have the serious disadvantage that the entire device must be placed in a freezer which often results in either the outer surface of the textile material becoming stuck to the freezer itself with likelihood of subsequent damage upon removal or frost is generated on the surface of the material which must be removed. In addition, there is the disadvantage that where cooling for a long period of time is desired, a plurality of separate complete frozen devices is necessary.

Applicant's device overcomes these aforementioned disadvantages associated with devices of the prior art by providing a device in the form of a elasticized or manually adjustable band of soft textile material which has at least one compartment with at least one opening into which individual bags or containers of frozen liquid or semi-liquid material are placed for use and subsequently removed when melted for refreezing and reuse. The band can be washed when necessary and also re-used.

Applicant's device of the present invention is particularly suited to be worn around the head or wrists to thereby reduce body heat and absorb perspiration of those engaged in physical effort such as sport participants and workers. This device is also suited for cooling various parts of the body for medical purposes.

It is therefore the primary object of the present invention to provide a new and improved coolant device with a wider range of uses, more convenience, and also complete mobility.

It is also an object of the present invention to provide a coolant device in the form of a band having at least one compartment into which can be placed sealed, refreezable liquid or semi-liquid filled containers.

It is a still further object of this invention to provide a coolant device utilizing individually sealed containers each filled with a freezable liquid or semi-liquid material.

It is yet another object of this invention to provide a coolant device wherein the individual sealed containers are linked together which both enables a plurality of the containers to conform to the contour of various parts of the anatomy or be separated from each other if more or less cooling is desired.

It is a still further object of this invention to provide a coolant device utilizing pre-sealed, freezable, liquid or semi-liquid filled containers which can be quickly and easily taken from a freezer or portable insulated cooler and inserted in one or more recesses in the device.

The invention will be hereinafter considered and described in detail and in connection with the accompanying drawings which illustrate the preferred embodiments of the invention.

BRIEF DESCRIPTION OF THE DRAWINGS

FIG. 1 is a perspective view of the coolant band of the present invention as worn on a person's head;

FIG. 2 is a perspective view of the coolant band revealing the pocket for receiving and storing a container of frozen liquid or semi-liquid material;

FIG. 3 is a cross sectional view of the coolant band taken along the lines 3—3 of FIG. 2;

FIG. 4 is a cross sectional view of the coolant band taken along the lines 4—4 of FIG. 2;

FIG. 5 is a perspective view of the linked containers having freezable liquid or semi-liquid used in the band of the invention;

FIG. 6 is a cross sectional view of a part of another embodiment of the band of the present invention;

FIG. 7 is a cross sectional view of a part of another embodiment of the band of the present invention; and FIG. 8 is a cross sectional view of a part of a further embodiment of the band of the present invention.

DESCRIPTION OF SPECIFIC EMBODIMENTS

Referring to FIGS. 1 through 5, the coolant band of the present invention is shown generally at 10 comprising an annular shaped band 12 of terry cloth or other absorbent textile material in as many layers as desired. I have shown the band 12 in a form in which the fabric is arranged in two layers, the first layer 14 having an uninterrupted surface 16 and the second layer 18 having a surface 20 wherein the ends of the fabric are joined to a strip 22 of elastometric material such as fabric covered rubber as can best be seen by referring to FIG. 4. The elastometic strip 22 maintains the surface 20 and the band 12 in general in direct contractive engagement with the part of the anatomy to be cooled. The strip 22 may, of course, extend around the entire surface 20 or, as shown in FIG. 2, only extend a portion of the distance. The elastometic material 22 may be woven, knitted or otherwise made a part of the fabric construction. The band may also be held in engagement with the part of the anatomy to be cooled by means of a manually adjustable strap or the like 23 shown in FIG. 8.

In the embodiment of the coolant band 12 shown in FIG. 2, a rectangular shaped strip 24 of soft absorbent textile material is connected by stitching 26 along three of its sides to the surface 20 of second layer 18 to thereby form a pocket 28. The stitching 26 also extends inwardly a distance 26(a) from the ends of the strip 24 for a reason to be discussed later.

The coolant for the band 12 is provided by means of a plurality of containers or bags 30 formed of water impermeable material such as a plastic film. The containers 30 are filled with a liquid material or a semi-liquid or gel-like material 32 at the time of manufacture and are hermetically sealed. The containers 30 are connected by a length of flexible plastic 34 in link fashion. Linking the containers 30 enables a plurality of same to easily bend to conform to the shape of the part of the body to be cooled. Linking the containers 30 also permits their easy separation from each other when just a specific number are required to cover the desired area. Normally, when the liquid material 32 is plain frozen water, articulation of the linked containers is provided by the length of flexible plastic 34 which connects the containers. If, however, more flexibility is desired, the material 32 can be, for example, a gel or a solution of propylene glycol and water or brine which turns into a semi-liquid slush when cooled.

The linked containers 30, are, when removed from the freezer in their frozen state, inserted into pocket 28 such that the end most containers are positioned beneath the extended stitching 26(a) as can best be seen by referring to FIG. 2. The extended stitching 26(a) served to retain the containers 30 in the pocket 28 during movement of the band 12.

The uninterrupted surface 16 of first layer 14 can be provided with an adhesive stip 38 sewn or otherwise secured thereto as shown in FIG. 6. The adhesive strip 38 would permit the attachment of the band 12 to sunvisors and the like (not shown) or would permit the band 12 to be attached to the inside of hats, helmets, caps or other headgear and the like.

In another embodiment of the coolant band 12 as shown in FIG. 7, at least one vertically extending slit 36 is provided in the second layer 18 through which the linked containers 30 can be slipped. The layers 14, 18 support the linked containers 30 and no separate pocket such as 28 is thus required. The extra effort required by the user to feed the containers through the slit 36 would be possibly compensated for by the reduced cost of the overall band 12 resulting from the absence of the pocket 28.

Another embodiment of the coolant band 12 is shown in FIG. 8 which comprises an outer layer 40, an intermediate layer 42 adjacent thereto and an inner layer 44 forming a tunnel-like pocket 46 for receiving the linked containers 30. The double layer of fabric 40, 42 aids significantly in insulating the containers 30 against externally applied heat from the environment thus extending the duration of the effective cooling of the containers. In the embodiment disclosed in FIG. 8, a single piece of fabric is used which is folded on itself to form the double layer 40, 42 and tunnel-like pocket 46. The layers are secured to each other at points 48. However, any one or all of the layers 40, 42, 44 may be separate pieces of fabric sewn together if desired. If layer 44 is shorter than 40 and 42, at least one opening for insertion of containers will be provided at each vertical end of shortened layer 44.

Also at least one horizontally extending slit 50 can be provided in the inner layer 44 to the tunnel 46 to enable the linked containers 30 to be quickly and easily inserted and removed. It being understood, of course, that the horizontal-type slit 50 can be used on the embodiment of FIG. 7 and the vertical-type slit 36 can be used on the embodiment of FIG. 8. The buckle and strap 23 can also be used on any other embodiments to provide a manually adjustable means to keep the coolant band 12 in contractive engagement with the part of the anatomy to be cooled.

It should be understood, of course, that the overall length and number of pocket 28 can vary depending on the extent of the area of the anatomy to be cooled.

In use, a plurality of sets each having the desired number of containers 30 are placed in a freezer or freezing compartment of a conventional refrigerator. When frozen and needed, a set of the containers 30 are removed from the freezer and inserted in either the pocket 28 of tunnel 46 or slit 36. The band is then positioned around the part of the body to be cooled. When the ice in the container 30 has melted, the band can be removed from the body and the warm container returned to the freezer. A new set of containers can then be inserted and activity resumed. When the band is no longer required, the container set can be returned to the freezer for refreezing and reuse and the band can be permitted to dry or be washed. Both the band 12 as well as the container sets 30 can thus be reused continuously.

In the foregoing description, a number of different embodiments of the present invention have been set forth. Other modifications and variations of the present invention as hereinbefore set forth may be made without departing from the spirit and scope thereof. Accordingly, only such limitations should be imposed as are indicated in the appended claims.

I claim:

1. A coolant band comprising:
   (a) an annular strip of textile material consisting of a first layer having an outwardly presented surface thereon and a second layer having an inwardly presented surface thereon, said first and second layers of material forming a pocket means therebetween,
   (b) coolant means containing a freezable liquid or semi-liquid material in said pocket means;
   (c) slit means in said inwardly presented surface of said second layer of textile material to form an opening for insertion and removal of said coolant means into said pocket means; and
   (d) means associated with said strip to maintain said inwardly presented surface and said pocket in direct contractive engagement with a part of the anatomy to be cooled.

2. A coolant band comprising:
   (a) an annular strip of textile material comprising at least a first layer having an outwardly presented surface thereon and a second layer having an inwardly presented surface thereon, said first and second layers of material forming a pocket means therebetween,
   (b) coolant means containing a freezable liquid or semi-liquid material in said pocket means;
   (c) slit means located exclusively in said inwardly presented surface of said second layer of textile material to form an opening for insertion and removal of said coolant means into said pocket means; and
   (d) means associated with said strip to maintain said inwardly presented surface and said pocket in direct contractive engagement with a part of the anatomy to be cooled.

3. A coolant band as set forth in claim 2 wherein said annular strip further comprises a third layer contiguous to and engaging the inner surface of said first layer, said pocket means being formed between said second and third layers.

\* \* \* \* \*